United States Patent
Morarie (10) Patent No.: US 11,376,156 B1
(45) Date of Patent: Jul. 5, 2022

(54) CONTACT LENS APPLICATOR

(71) Applicant: Mark Morarie, Broomfield, CO (US)

(72) Inventor: Mark Morarie, Broomfield, CO (US)

( * ) Notice: Subject to any disclaimer, the term of this patent is extended or adjusted under 35 U.S.C. 154(b) by 36 days.

(21) Appl. No.: 17/160,160

(22) Filed: Jan. 27, 2021

(51) Int. Cl.
*A61F 9/00* (2006.01)

(52) U.S. Cl.
CPC .................................. *A61F 9/0061* (2013.01)

(58) Field of Classification Search
CPC ...................... A61F 9/0061; A61F 2009/0035
USPC ........................................... 294/1.2; 206/5.1
See application file for complete search history.

(56) References Cited

U.S. PATENT DOCUMENTS

| | | | | |
|---|---|---|---|---|
| 3,063,083 | A * | 11/1962 | Obitts | B25B 9/02 294/1.2 |
| 3,304,113 | A * | 2/1967 | Hutchison | A61F 9/0061 294/1.2 |
| 3,343,657 | A * | 9/1967 | Speshyock | A61F 9/0061 206/5.1 |
| 3,600,028 | A * | 8/1971 | Henning | A61F 9/0061 294/1.2 |
| 3,697,109 | A * | 10/1972 | Parrent | G02C 7/04 294/1.2 |
| 4,193,622 | A * | 3/1980 | Overman | A61F 9/0061 294/1.2 |
| 4,223,782 | A * | 9/1980 | Giambalvo | A45C 11/005 206/5.1 |
| 4,520,923 | A * | 6/1985 | Waldman | A45C 11/005 206/815 |
| 5,236,236 | A * | 8/1993 | Girimont | A61F 9/0061 294/1.2 |
| D339,970 | S * | 10/1993 | Marshall | D8/52 |
| 5,407,241 | A * | 4/1995 | Harrison | A61F 9/0061 294/1.2 |
| 9,913,751 | B2 * | 3/2018 | Hopper | A61F 9/0061 |

* cited by examiner

Primary Examiner — Paul T Chin (57) ABSTRACT

A contact lens applicator for applying a contact lens to an eye of a user includes a base member, a stand, and a lens holder. The base member includes an inner surface and retaining walls. The stand includes a first end, a second end, at least one leg, and a passageway. The lens holder includes a handle, a cup, and a passageway. The first end of the stand removably engages with the handle of the lens holder. The second end of the stand removably engages with the base member. The cup of the lens holder is configured to hold a contact lens. When the lens holder and the stand are removably engaged with the base member, the passageway of the stand and the passageway of the lens holder align above the base member, allowing natural light to pass through the passageways of the stand and the lens holder.

14 Claims, 7 Drawing Sheets

CONTACT LENS APPLICATOR

FIELD OF THE DISCLOSURE

The present disclosure generally relates to contact lens applicators and, more particularly, to a contact lens applicator that allows for a stable and guided application of a contact lens to a user's eye.

BACKGROUND

Most eye contact lenses are inserted manually into the eye using a user's finger. The contact lens is placed concave side upward on the user's finger and placed onto the eye. User's hands are often shaky and unstable, causing misalignment or requiring multiple attempts to insert the contact lens. User's are also sometimes nervous about touching their own eyeball with their finger, making the use of contact lenses an unpleasant experience.

Inserting contact lenses that are dry is uncomfortable and can irritate a user's eye, causing an imperfect fit onto the eye. Utilizing contact lens solutions is preferred to avoid the irritations and issues with dry contact lenses. But inserting contact lenses manually or with other applicator devices using liquid solutions can be a messy process, with liquid dripping down a user's face or resulting in messy countertops or floors.

Other contact lens applicators do not provide stability and alignment systems for the user to be able to effectively align the contact lens with their eye during insertion. This can cause misalignment. If other contact lens applicators do have an alignment system, it requires LED systems which can make the applicator expensive, or the alignment system is too small and not effective.

SUMMARY

The disclosed example of a contact lens applicator includes a base member, a stand, a lens holder, and a lid. The example contact lens applicator is cost effective by being manufactured using medical grade polycarbonate, and in some cases, medical grade silicone or latex materials. The base member can be configured to included an inner surface and retaining walls. The stand and lens holder can removably engage with the base member to create an elevated, steady, and natural light-guiding applicator or application kit for a contact lens, alleviating the need for the user to manually touch the contact lens during insertion. The user can instead focus on holding their eye open with both hands and/or multiple fingers while aligning with the contact lens on the contact lens applicator during insertion. The inner surface and retaining walls of the base member can hold any excess liquid that is released from the contact lens when being inserted into a user's eye.

The stand and the lens holder include passageways through both the stand and the lens holder that are aligned together when the stand and lens holder are engaged with the base member. The base member can include a raised portion that also aligns with the passageways of the stand and the lens holder when engaged with the base member, emphasizing a strong and consistent natural light tunnel through the stand and lens holder and further through the contact lens and to the user's eye in order for the user to effectively align their opened eye with the contact lens while hovering over the contact lens applicator and touching their eye to the contact lens.

The example contact lens applicator can further include a lid. The lid can be the same shape as the base member and be configured to fit around the retaining walls of the base member when engaged with the base member. When the stand and the lens holder are disengaged or disassembled from the base member, the stand and base member can fit within an inner cavity of the base member and the lid, for compact transport and to keep the components of the contact lens applicator together.

In some examples, the base member can be configured as a basin for fully retaining any excess liquid created from the preparation and application of a contact lens. In some examples, the stand can include one or more legs having one or more ridges on the legs. The legs can include bends that create points on the legs. The shape of the legs, along with the ridges, can assist in directing any excess liquid from the contact lens during preparation and application. The points in the legs, along with the ridges can be configured to direct the excess liquid into the base member or basin of the contact lens applicator and avoid liquid spilling outside of the base member onto external surfaces.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

One example of a contact lens applicator 100 is shown in FIGS. 1-7. The contact lens applicator 100 can be conveniently sized for mobility and travel applications and can be sized to secure and hold a single contact lens 700 during the application of the contact lens 700 onto a user's eye. The contact lens applicator 100 includes a base member 200, a stand 300, and a lens holder 400.

The contact lens applicator 100 can be used for a standard contact lens that fits the diameter of a user's cornea or with enlarged lenses, such as a scleral lens or hybrid lens. Scleral lenses are large diameter lenses, with sizes ranging from 14 mm to 24 mm in diameter. Scleral lenses extend beyond the cornea of a user's eye and rest on the sclera, or white part, of the eye. In comparison to corneal lenses, scleral lenses bulge outward more than corneal lenses. The space between the cornea and the scleral lens can be filled with lens solution, or artificial tears solutions. The example shown illustrates a contact lens applicator 100 for use with an enlarged contact lens 700.

In the example shown, the base member 200 includes an inner surface 202, an outer surface 204, and a plurality of retaining walls 206. In some examples, the base member 200 can be referred to a basin. In the example shown, the base member 200 is formed substantially as a square but in other examples the base member 200 can be formed as a different shape such as a rectangle, circle, or oval. The base member 200 includes a raised portion 208. The raised portion 208 is of a conical shape and is generally located in the center of the base member 200 extending from the inner surface 202. In other examples, the raised portion can be of a different shape: square, rectangular, or rounded.

The base member 200 includes one or more steps 210a and 210b that are used as connection points to removably engage the stand 300 to the base member 200. The steps can be generally located near the retaining walls 206 of the base member 200 and extend from the inner surface 202 of the base member 200. The steps 210a and 210b can include holes 214a and 214b. In the example shown, the steps 210a and 210b are formed as a rectangle, but in other examples can be of other shapes such as squares or circles. In the example shown, the steps 210a and 210b align with the raised portion 208 on the inner surface 202 of the base member 200, with the raised portion 208 centered between the steps 210a and 210b. This allows for the stand 300 to be positioned above the raised portion 208 of the base member 200 when the stand 300 is removably connected to the base member 200.

Figure 7:
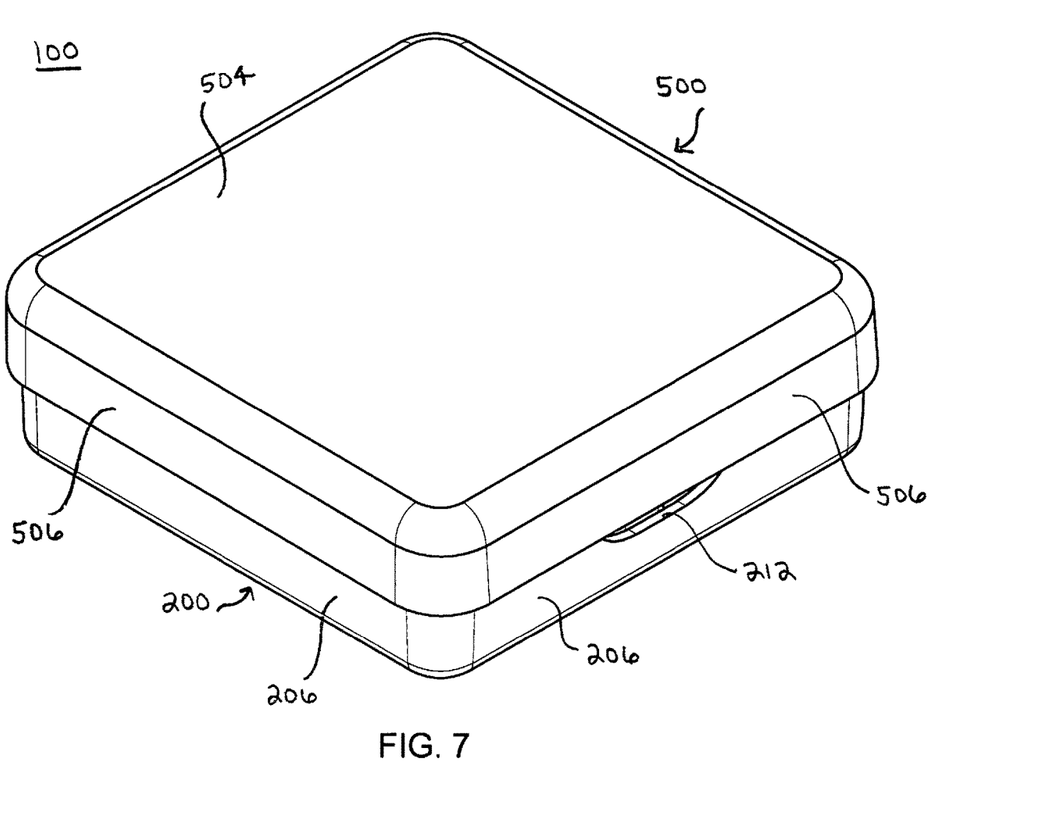
FIG. 7 is a perspective view of the example contact lens applicator.

The base member 200 also can include cut outs 212. As shown in FIG. 7, when a lid 500 is removably connected with the base member 200, the cut outs 212 of the base member 200 can be accessed for easy opening and removal of the lid 500 from the base member 200 by allowing a user's fingers to fit within the cut outs 212 and apply a pulling force to disengage the lid 500 from the base member 200. The cut outs 212 in this example are rounded curves, but in other examples can be of a different shape.

Figure 1:
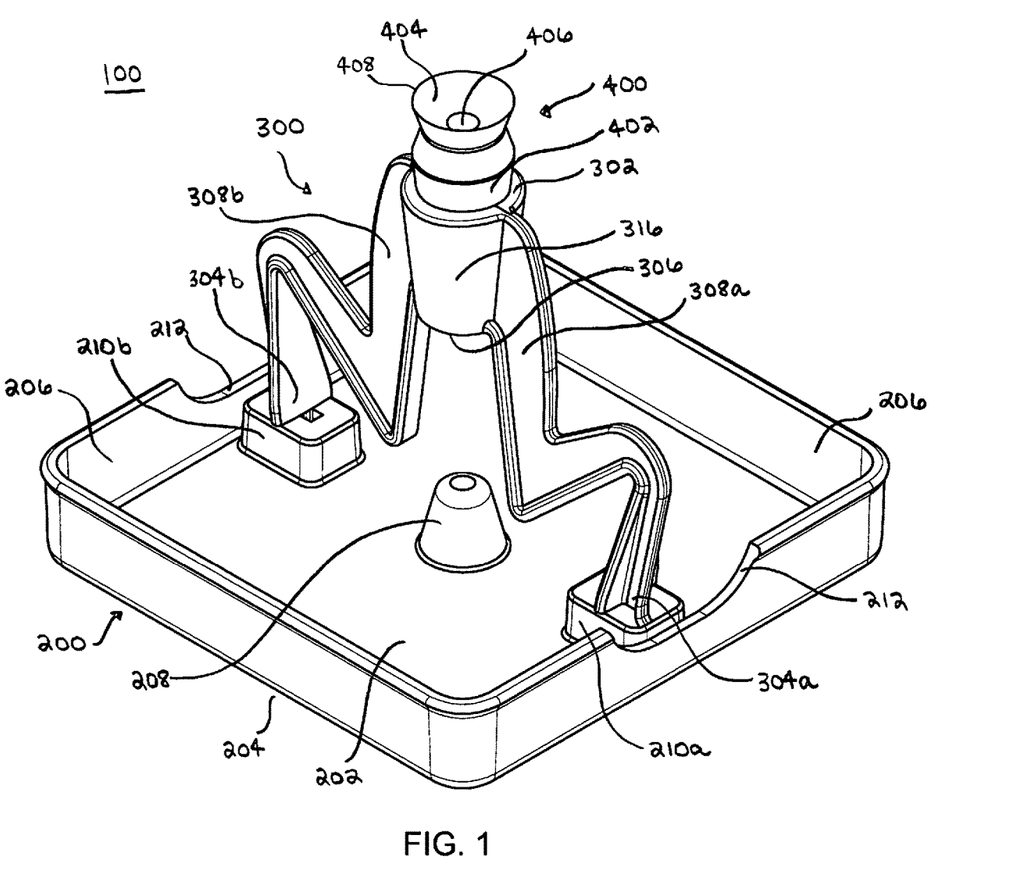
FIG. 1 is a perspective view of one example of a contact lens applicator.
Figure 2:
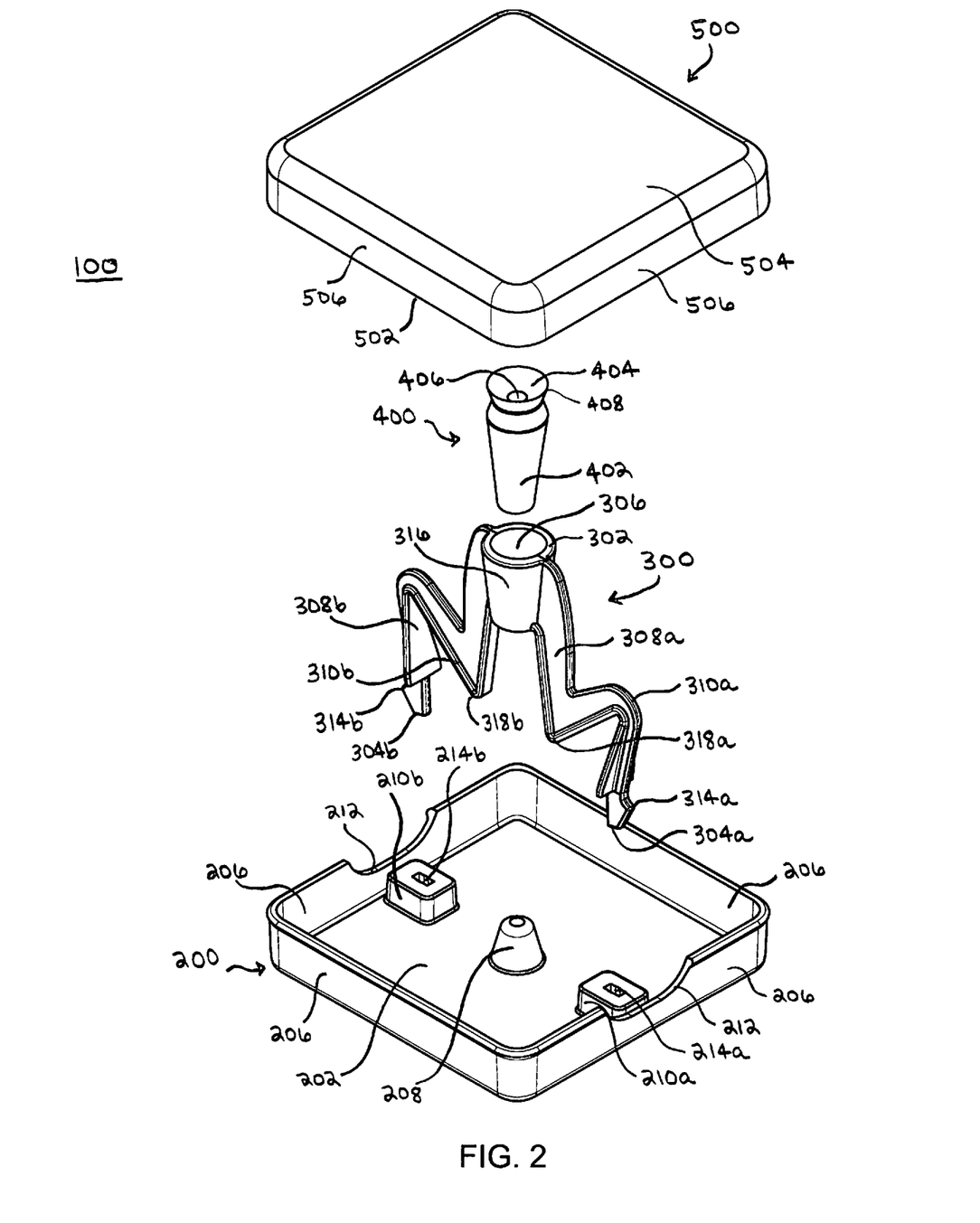
FIG. 2 is an exploded perspective view of the example contact lens applicator.

The stand 300 in the example shown includes a first end 302, a tube 316, a plurality of second ends 304a and 304b, a plurality of legs 308a and 308b, and a passageway 306. The second ends 304a and 304b of the stand 300 engage with the steps 210a and 210b of the base member 200 to removably connect the stand 300 to the base member 200 and position the stand 300 upright and away from the inner surface 202 of the base member 200. As shown in FIG. 2, the second ends 304a and 304b of the stand include tabs 314a and 314b. When the stand 300 is removably connected to the base member 200, tab 314a on the second end 304a engages and locks into the hole 214a of the step 210a of the base member 200. Similarly, tab 314b on the second end 304b engages with the hole 214b of the step 210b of the base member 200, locking the stand 300 upright and in place while connected to the base member 200. This allows for a solid and secure stand 300 when the outer surface 204 of the base member 200 is resting on a flat surface like a bathroom counter, a desk, or any type of counter. In some examples, the base member does not include steps and the legs engage with the inner surface of the base member directly. In even other examples, holes can be formed within the inner surface of the base member in which the legs of the stand removably engage.

The stand 300 can further include ridges 310a and 310b that extend along the legs 308a and 308b. The ridges 310a and 310b can provide rigidity and stability to the stand 300 when the stand 300 is engaged with the base member 200, preventing the stand 300 from falling one way or another while removably connected to the base member 200.

In the example shown, the tube 316 of the stand 300 extends from the first end 302 towards the second ends 304a and 304b. The tube 316 can be tapered and allows for the passageway 306 to extend through the first end 302 of the stand 300 and in this example in between the legs 308a and 308b of the stand 300. When the stand 300 is connected to the base member 200, the center of the tube 316 of the stand 300 aligns above the raised portion 208 of the base member 200. In the example shown, there is space between the raised portion 208 of the base member 200 and the tube 316 of the stand 300, allowing for natural or ambient light to pass through the passageway 306 of the tube 316 while the stand 300 is connected to the base member 200. The amount of light passing through the passageway 306 of the tube 316 is intensified with the raised portion 208 of the base member 200. The amount of space between the raised portion 208 and the tube 316 can vary between examples. When the user 600 hovers above the contact lens applicator 100, the raised portion 208 of the base member 200 can be seen through the passageway 306 of the stand 300.

In the example shown, the stand 300 includes two legs 308a and 308b. In other examples, the stand can include only one leg or more than two legs, with corresponding ends, tabs, and ridges. The legs 308a and 308b can be configured with multiple bends as they connect the first end 302 with the second ends 304a and 304b of the stand 300. One or more bends in the legs 308a and 308b can form points 318a and 318b of the stand 300. In some examples, the ridges 310a and 310b along the legs 308a and 308b can also act as a channel along the legs 308a and 308b of the stand 300.

Figure 5:
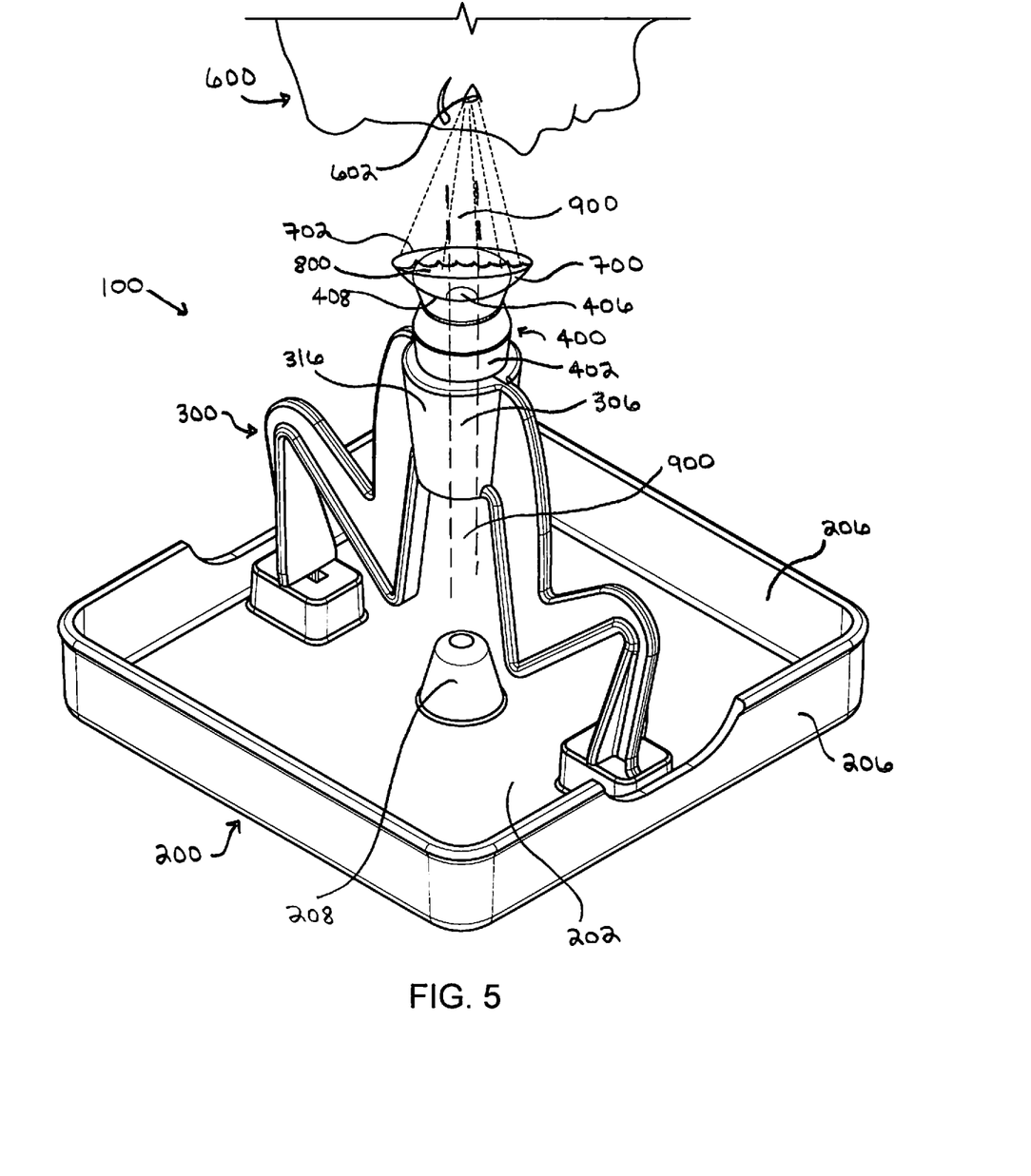
FIG. 5 is a perspective view of the example contact lens applicator, positioned below a user's face and eye.

As shown in FIG. 5, when excess liquid spills out of the contact lens 700 while preparing the contact lens 700 on the applicator for insertion into the user's eye 602 or while the user 600 inserts the contact lens 700 into their eye 602, excess liquid can flow down around the lens holder 400, down along the stand 300 and along the legs 308a and 308b and the ridges 310a and 310b of the stand. The excess liquid can then drip from the legs 308a and 308b at the points 318a and 318b of the stand 300 and onto the inner surface 202 of the base member 200. This allows for the base member 200 to collect all excess liquid and prevent liquid from spilling out of the base member 200 onto the external surface that the outer surface 204 of the base member 200 of the contact lens applicator 100 is resting on. When the user is finished with the contact lens applicator 100, the excess liquid collected within the base member 200 can be discarded or wiped out without having the liquid spill unintentionally onto counters, floors, or other surfaces that the contact lens applicator 100 is resting on.

When the contact lens applicator 100 is not in use, legs 308a and 308b of the stand 300 are formed substantially of a rigid material yet flexible enough to squeeze the legs 308a and 308b together to disengage the tabs 314a and 314b from the holes 214a and 214b of the steps 210a and 210b of the base member 200. The stand 300 is sized to then be able to lay flat on the inner surface 202 of the base member 200, fitting within the retaining walls 206 of the base member 200.

As shown in the example, the lens holder 400 includes a handle 402 and a cup 404. The lens holder 400 can also be referred to as a plunger. The lens holder 400 further includes a passageway 406 that extends the entire length of the lens holder 400, through the handle 402 and through the cup 404. In the example shown, the handle 402 has a tapered shape. The handle 402 of the lens holder 400 fits into and rests within the tube 316 of the stand 300. When the stand 300 is removably connected to the base member 200, the handle 402 of the lens holder 400 rests within the tube 316 of the stand 300 with the concave side of the cup 404 of the lens holder 400 facing away from the inner surface 202 of the base member 200.

In the example shown, when the lens holder 400 is engaged with the stand 300, the passageway 406 of the lens holder 400 aligns with the passageway 306 of the stand 300. When the user 600 looks from above and over the contact lens applicator 100, the raised portion 208 of the base member 200 can be seen through the aligned passageway 306 of the stand 300 and the passageway 406 of the lens holder 400. In some examples, the base member 200 does not include a raised portion 208 and when looking from above and over the contact lens applicator the inner surface 202 of the base member 200 can be seen through the passageway 306 of the stand 300 and the aligned passageway 406 of the lens holder 400.

The lens holder 400 can be made of high-grade or medical grade latex rubber or silicone. It is preferred that the lens holder 400 has enough elasticity for a user to at times be able to pinch the handle 402 of the lens holder 400. In some instances, a user of the lens holder 400 can utilize the lens holder 400 separately from the contact lens applicator 100 to remove contact lenses from their eyes by pinching the handle 402 of the lens holder 400. This pinching or squeezing will close the passageway 406 of the lens holder 400. When the handle 406 of the lens holder 400 is pinched, a user can then touch the cup 404 of the lens holder 400 against the inserted contact lens 700 on their eye 602. By carefully releasing some or all of the pressure from the pinching or squeezing of the handle 406, the contact lens 700 will adhere to the soft cup 404 of the lens holder 400, matching the concave shape of the cup, and come off of the eye.

As shown in FIG. 2, and in FIG. 7, the contact lens applicator 100 can include a lid 500. The lid can include an inner surface 502, an outer surface 504, and walls 506. The lid 500 can be of the same shape and size as the base member 200, with the walls 506 of the lid 500 configured to extend around the retaining walls 202 of the base member 200. In some examples, the contact lens applicator 100 can be referred to a contact lens application kit. The contact lens application kit can include the base member, the stand, the lens holder, and the lid, with the stand and the lens holder fitting inside an inner cavity created by the inner surface 202 and retaining walls 206 of the base member 200 and the inner surface 502 of the lid 500 when the lid 500 is connected onto the base member 200.

Figure 3:
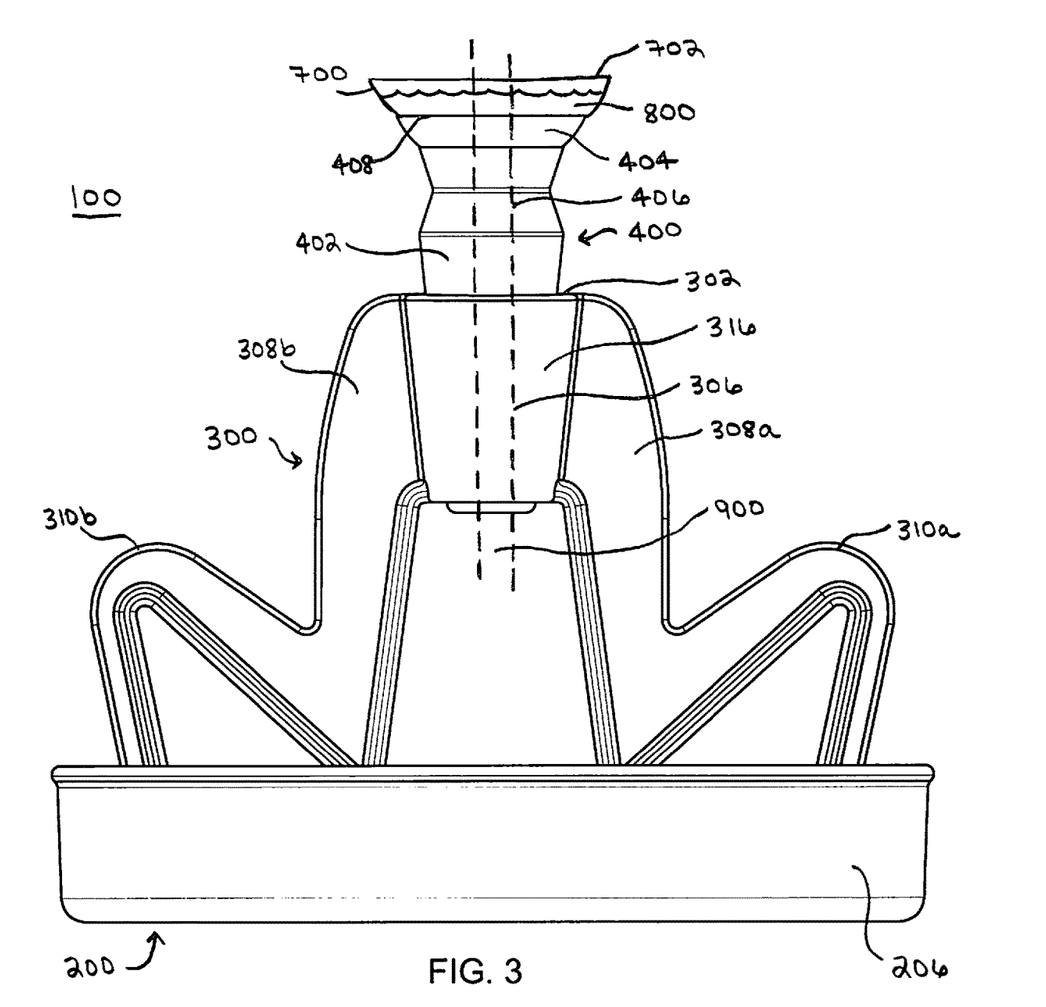
FIG. 3 is a side elevation view of the example contact lens applicator.

FIG. 3 shows a side elevation view of the example contact lens applicator 100. The base member 200 can be seen in a horizontal position as if it were resting on a surface, such as a bathroom counter, a desk, or other flat surface. The stand 300 is engaged with the base member 200 as described previously and secured in an upright position. The lens holder 400 is engaged with the stand 300, with the handle 402 of the lens holder 400 resting within the tube 316 of the stand 300. The lens holder 400 resting within the tub 316 of the stand allows for the cup 404 of the lens holder to be horizontal from the side elevation view. When the contact lens 700 is then placed on the cup 404, with the concave portion of the contact lens 700 matching with the concave portion of the cup 404, liquid 800 or solution can be added to the contact lens 700 while the contact lens 700 is resting on the cup 404 of the contact lens applicator 100.

When the contact lens 700 is resting on the cup 404 of the contact lens applicator 100, it is raised above the external surface that the outer surface 204 of the bottom member 200 is resting on. The distance that the resting contact lens 700 is from the external surface that the bottom member 200 is resting on can vary, and in this example there is enough distance so that when the user 600 hovers over the contact lens applicator 100 and begins to get closer to the contact lens applicator 100 in order for the user's eye 602 to connect with the contact lens 700, other portions of the user's face, such as their nose do not make contact with the base member 200 or the surface that the base member 200 is resting on. This allows for a more comfortable and elevated insertion experience, but keeps the contact lens applicator 100 small enough for portability and travel.

The dotted lines of FIG. 3 through the contact lens applicator 100 represent the light tunnel 900 created by the passageway 306 of the stand and the passageway 406 of the lens holder. As shown, both passageways 306 and 406 align when the lens holder 400 is engaged with the stand 300 and the stand is secured onto the base member 200. When a user hovers above the contact lens applicator 100, the user can look through the passageway 406 of the lens holder 400 and the passageway 306 of the stand 300 and see the bottom member 200 through both the lens holder 400 and the stand 300. In this example, with the raised portion 208 of the bottom member 200 also aligned with the passageways 306, 406, of the stand 300 and lens holder 400, the user can see the top of the raised portion 208 of the base member 200 through the stand 300 and lens holder 400 when looking through the aligned passageways.

Figure 4:
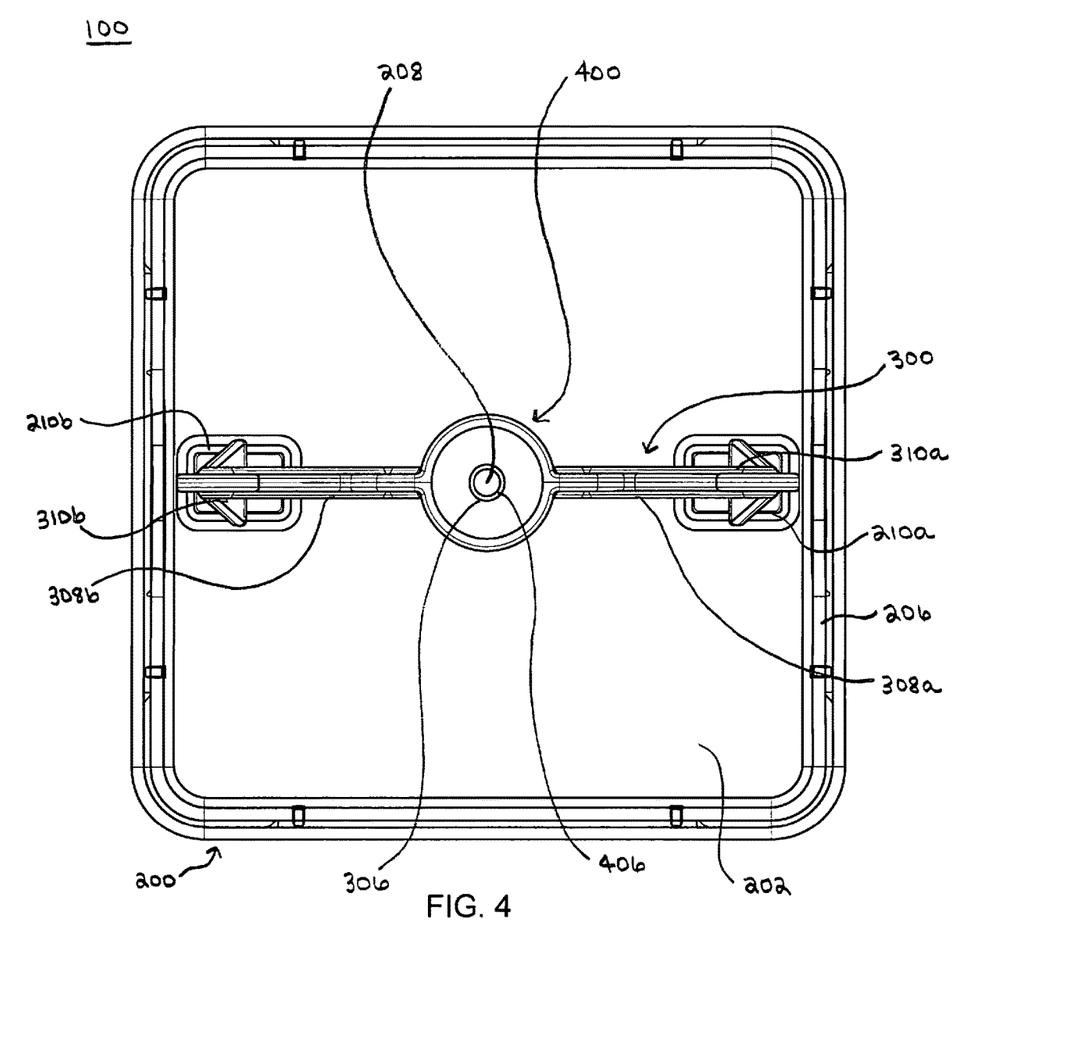
FIG. 4 is a top view of the example contact lens applicator.

FIG. 4 shows a top view of the example contact lens applicator 100, and further shows the alignment of the passageway 306 of the stand 300 and the passageway 406 of the lens holder 400 when the stand 300 is removably connected to the base member 200. When looking through the aligned passageway 306 of the stand 300 and passageway 406 of the lens holder 400, a user can see the raised portion 208 of the base member 200. When the contact lens 700 is resting on the cup 404 of the lens holder 400, and filled with liquid 800, the user 600 can still see the raised portion 208 of the base member 200 and the natural light tunnel 900 that is created through the passageways 306, 406 of the stand 300 and the lens holder 400. This light tunnel 900 assists the user 600 in guiding their opened eye 602 to the center of the resting contact lens 700 and assist with centering the contact lens 700 around the cornea of the eye 602. With the resting contact lens 700 stabilized and elevated on the contact lens applicator 100, the user 600 is able to focus on keeping their eye open with multiple fingers and both hands if needed, making for a more comfortable insertion experience.

FIG. 5 shows a perspective side view of the example contact lens applicator 100. The base member 200 is configured to be resting on a flat surface. The stand 300 is removably secured to the base member 200. The lens holder 400 is engaged with the stand 300, the handle 402 of the lens holder 400 resting within the tube 316 of the stand 300. The contact lens 700 is resting on the cup 404 of the lens holder 400. Liquid 800 is added into the concave portion of the contact lens 700. In this example, the diameter 408 of the cup 404 is smaller than the diameter 702 of the contact lens 700. The user 600 is shown hovering above the contact lens applicator 100, with the user's eye 602 facing the contact lens applicator 100 and hovering over the aligned passageway 306 of the stand and the passageway 406 of the lens holder 400. The user 600 can then align their eye 602 with the light tunnel 900 created by the passageway 306 of the stand and the aligned passageway 406 of the lens holder and lower their eye towards the resting contact lens 700 and guide the contact lens 700 onto their open eye 602. Excess liquid from the insertion process can again drain down the lens holder 400, down the stand 300 and along the ridges 310a and 310b of the stand 300, and drip from the points 318a and 318b of the legs 308a and 308b of the stand 300 and onto the inner surface 202 of the base member 200.

Figure 6:
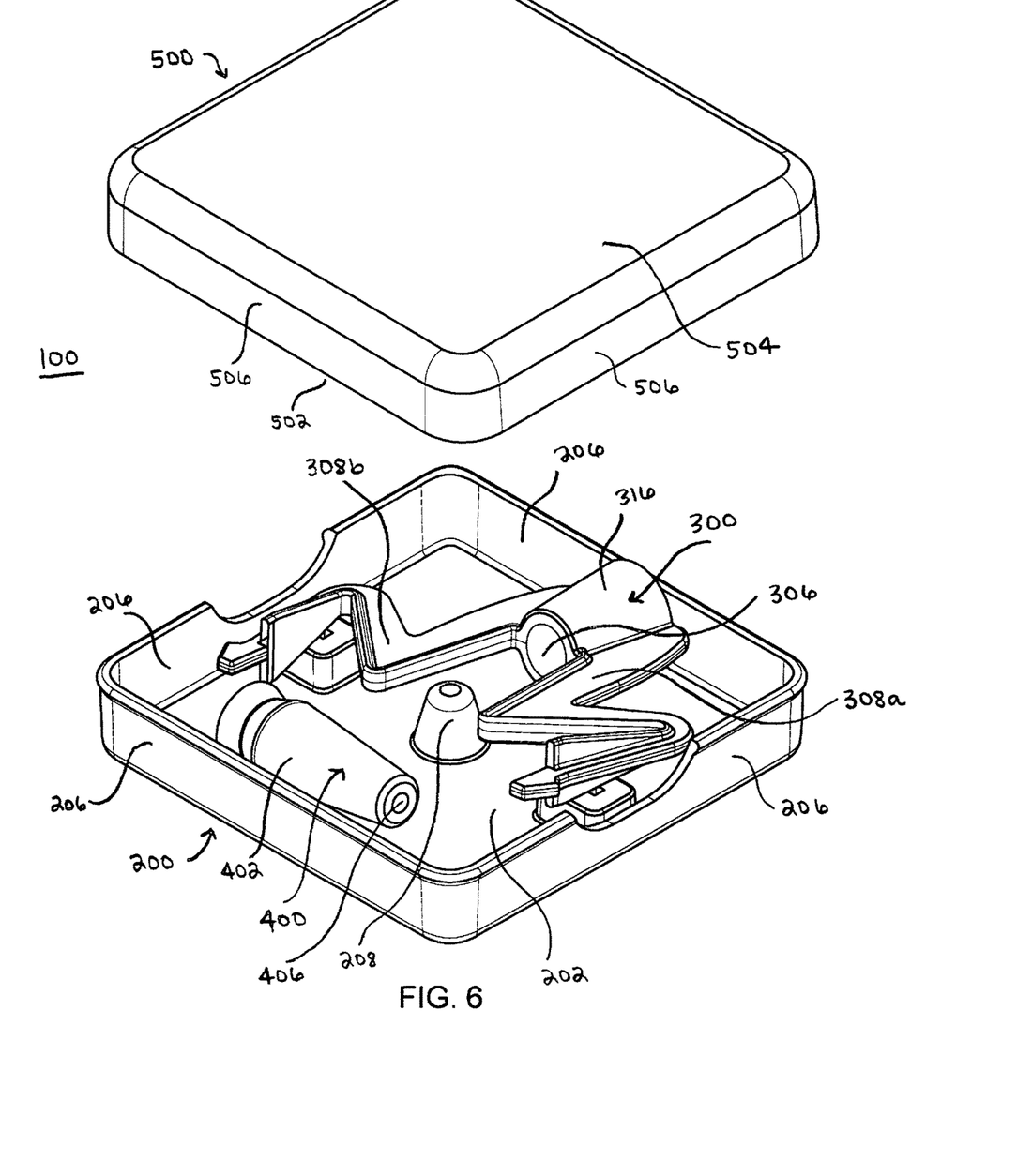
FIG. 6 is a perspective view of the example contact lens applicator.

FIG. 6, and FIG. 7, show perspective views of the example contact lens applicator 100 in a disassembled state. The stand 300 is disengaged from the base member 200 and the lens holder 400 is disengaged from the stand 300. In this example, when the contact lens applicator 100 is not in use the stand 300 can be laid down within the inner surface 202 and retaining walls 206 of the base member 200. The lens holder 400 can also be laid down within the inner surface 202 and retaining walls 206 of the base member, near and not interfering with the stand 300. With the stand 300 and lens holder 400 disengaged and within the base member 200, the lid 500 can cover the stand 300 and the lens 400, surround the retaining walls 206 of the base member 200 and form an inner cavity for the stand 300 and lens holder 400 to be stored when not in use. This can ease transport of the contact lens applicator 100, and keep the components of the contact lens applicator 100 together and secure.

The contact lens applicator 100 can also be referred to as a contact lens application kit. The contact lens application kit includes the base member 200, the stand 300, the lens holder 400, and the lid 500. The contact lens applicator, or application kit, can further include other accessories that fit within the inner cavity created by the inner surface 202 and the retaining walls 206 of the base member 200, and the lid 500. These other accessories can include a compartment for holding one or more contact lenses, tweezers or more specifically soft-tipped tweezer for transporting a contact lens from a compartment to the cup of the contact lens applicator. Other accessories could include a vial or area of the inner cavity for holding liquid or solutions for use with the insertion of the contact lens to the user's eye.

Those skilled in the art will recognize that a wide variety of modifications, alterations, and combinations can be made with respect to the above-described examples without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s).

What is claimed is:

1. A contact lens applicator for applying a contact lens to an eye of a user, comprising:
    a base member having an inner surface, an outer surface, and retaining walls, the retaining walls defined by the inner surface and the outer surface of the base member;
    a stand having a first end, a second end, a first leg configured to connect the first end and the second end, a tube extending from the first end, and a passageway through the tube, the second end of the stand configured to removably engage with the inner surface of the base member; and
    a lens holder having a handle, a cup, and a passageway through the handle and the cup, the cup configured to support the contact lens, the handle configured to removably engage with the tube of the stand,
    wherein the passageway of the stand and the passageway of the lens holder align when the stand and the lens holder are removably engaged with the base member.

2. The contact lens applicator of claim 1, wherein the base member includes a raised portion on the inner surface, wherein the raised portion of the base member aligns with the passageway of the stand and the passageway of the lens holder when the stand and the lens holder are removably engaged to the base member.

3. The contact lens applicator of claim 2, wherein the raised portion on the inner surface of the base member is conical.

4. The contact lens applicator of claim 1, wherein the tube of the stand is tapered.

5. The contact lens applicator of claim 4, wherein the handle of the lens holder is tapered.

6. The contact lens applicator of claim 1, wherein the stand further includes a second leg connecting the first end of the stand and a third end of the stand.

7. The contact lens applicator of claim 6, wherein the stand further includes one or more ridges extending along at least one of the first leg or the second leg of the stand.

8. The contact lens applicator of claim 1, wherein a diameter of the cup of the lens holder is smaller than a diameter of the contact lens.

9. The contact lens applicator of claim 1, wherein the outer surface of the base member rests horizontally on an external surface and the cup of the lens holder supports the contact lens so that a liquid solution can be added into the contact lens.

10. A contact lens application kit, comprising:
    a base member having an inner surface and retaining walls;
    a lid having walls configured to extend around the retaining walls of the base member;
    a stand having a tube and a plurality of legs, the plurality of legs configured to removably engage with the inner surface of the base member; and
    a lens holder configured to removably engage with the tube of the stand,
    wherein the stand and the lens holder, when disengaged from the base member, can fit within an inner cavity of the base member and the lid when the lid is removably engaged with the base member.

11. The contact lens application kit of claim 10, the inner cavity of the base member and the lid further comprising an area configured to hold an accessory.

12. The contact lens application kit of claim 11, wherein the accessory is a storage compartment for one or more contact lenses.

13. The contact lens application kit of claim 11, wherein the accessory is a vial of liquid solution.

14. The contact lens application kit of claim 11, wherein the accessory is a soft-tipped tweezer.

* * * * *